United States Patent
Ristol Debart et al.

(10) Patent No.: US 10,358,462 B2
(45) Date of Patent: Jul. 23, 2019

(54) METHOD FOR THE PREPARATION OF IMMUNOGLOBULINS

(71) Applicant: Instituto Grifols, S.A., Parets del Vallès (ES)

(72) Inventors: Pere Ristol Debart, Parets del Vallès (ES); Salvador Grancha Gamon, Parets del Vallès (ES); Juan Ignacio Jorquera Nieto, Parets del Vallès (ES); Maria Mercedes Faro Tomas, Parets del Vallès (ES); Nuria Jorba Grifols, Parets del Vallès (ES)

(73) Assignee: INSTITUTO GRIFOLS, S.A., Parets del Vallès (Barcelona) (ES)

( * ) Notice: Subject to any disclaimer, the term of this patent is extended or adjusted under 35 U.S.C. 154(b) by 313 days.

(21) Appl. No.: 15/276,544

(22) Filed: Sep. 26, 2016

(65) Prior Publication Data

US 2017/0198009 A1    Jul. 13, 2017

(30) Foreign Application Priority Data

Aug. 31, 2015 (ES) .................. P201531243

(51) Int. Cl.

| | |
|---|---|
| *C07K 16/06* | (2006.01) |
| *C07K 16/00* | (2006.01) |
| *A61K 39/395* | (2006.01) |
| *C07K 1/34* | (2006.01) |
| *C12N 7/00* | (2006.01) |

(52) U.S. Cl.
CPC .......... *C07K 1/34* (2013.01); *A61K 39/39516* (2013.01); *C07K 16/00* (2013.01); *C07K 16/06* (2013.01); *C07K 16/065* (2013.01); *C12N 7/00* (2013.01); *C12N 2770/24363* (2013.01)

(58) Field of Classification Search
None
See application file for complete search history.

(56) References Cited

U.S. PATENT DOCUMENTS

| | | | | |
|---|---|---|---|---|
| 4,164,495 A | * | 8/1979 | Hansen | ................ C07K 16/065 530/363 |
| 4,880,913 A | * | 11/1989 | Doleschel | ............ C07K 16/065 530/390.5 |
| 6,281,336 B1 | * | 8/2001 | Laursen | ........... A61K 39/39591 424/176.1 |
| 9,200,032 B2 | * | 12/2015 | Ristol Debart | .. A61K 39/39525 |

FOREIGN PATENT DOCUMENTS

| | | |
|---|---|---|
| EP | 0 893 450 A1 | 1/1999 |
| JP | H11-29494 A | 2/1999 |
| JP | 2007-533660 A | 11/2007 |
| JP | 2008-500959 A | 1/2008 |
| WO | WO 2005/073252 A1 | 8/2005 |
| WO | WO 2005/082937 A2 | 9/2005 |
| WO | WO 2015/056237 A2 | 4/2015 |
| WO | WO 2015/056237 A3 | 4/2015 |
| WO | WO 2016/073401 A1 | 5/2016 |

OTHER PUBLICATIONS

Lucena et al. "A new methodoloy for polyvalent intravenous immunoglobulin solution production with a two-stage process of viral inactivation" Brazilian J of Pharmaceutical Sciences, 46(4), 2010 (Year: 2010).*
Office Action, dated Jan. 17, 2018, in European Application No. 16159748.9.
Office Action, dated Mar. 13, 2018, in Japanese Patent Application No. 2016-186988.
Extended European Search Report dated Dec. 1, 2016 in Application No. 16159748.9.
Wu et al., Plasma-derived IVIG Optimising IVIG Manufacturing Around Established Precipitation Techniques Introduction, XP55321789, Retrieved from the Internet: URL:https://www.pall.com/pdfs/Biopharmaceuticals/Poster_IVIG_TechPoster.pdf; Dec. 12, 2013; [retrieved on Nov. 22, 2016].

* cited by examiner

*Primary Examiner* — Daniel E Kolker
*Assistant Examiner* — James L Rogers
(74) *Attorney, Agent, or Firm* — Knobbe, Martens, Olson & Bear, LLP

(57) ABSTRACT

The present invention relates to a method for the preparation of a solution of immunoglobulins based on an initial solution of immunoglobulins with a purity greater than or equal to 96% in the presence of a polyether or polymer of glycol, characterized in that it comprises the steps of: a) adding caprylic acid or salts of the same to the initial solution; b) adjusting the pH of the solution obtained in step a); c) incubating the solution obtained in step b) for the time and at a temperature necessary for the inactivation of enveloped viruses; d) performing a step of ultrafiltration/diafiltration on the solution obtained in step c).

21 Claims, No Drawings

METHOD FOR THE PREPARATION OF IMMUNOGLOBULINS

CROSS REFERENCE TO RELATED APPLICATIONS

This application claims the benefit of priority of the Spanish Patent Application No. P201531243, filed Aug. 31, 2015, which is hereby incorporated by reference in its entirety.

BACKGROUND

Field

The present invention relates to a new method for the preparation of immunoglobulins. The immunoglobulin composition obtained is suitable, for example, for parenteral administration.

Description of Related Art

Immunoglobulins are glycoproteins that can be found in soluble form in the blood and other body fluids of vertebrates, and are used by the immune system to identify and neutralise foreign bodies such as bacteria, viruses or parasites. Immunoglobulins have various medical applications such as the diagnosis of diseases, therapeutic treatments and prenatal therapy. The most common therapeutic applications of immunoglobulins can be classed in three general groups of pathologies: primary immunodeficiencies (humoral immune deficiency), secondary immunodeficiencies or acquired immunodeficiencies (for example, in the prevention and treatment of virus infections) and autoimmune immunodeficiencies (development of antibodies).

SUMMARY

In some embodiments, a method for the preparation of a solution of immunoglobulins based on an initial solution of immunoglobulins with a purity greater than or equal to 96% in the presence of a polyether or polymer of glycol is provided. In some embodiments, the method comprises the steps of: a) adding caprylic acid or salts of the same to the initial solution; b) adjusting the pH of the solution obtained in step a); c) incubating the solution obtained in step b) for a time and at a temperature necessary for the inactivation of enveloped viruses; and d) performing a step of ultrafiltration/diafiltration on the solution obtained in step c).

In some embodiments, the method also comprises a step of final formulation of the solution of immunoglobulins obtained in step d).

In some embodiments of the method, the initial solution of immunoglobulins is derived from fraction I+II+III, fraction II+III or fraction II, obtained according to the Cohn or Cohn-Oncley method, or from precipitate A or I+A or GG, obtained according to the Kistler-Nitschmann method, or variations on the same, which have been additionally purified to obtain a purity greater than or equal to 96% of IgG.

In some embodiments of the method, the initial solution of immunoglobulins is derived from fraction II+III obtained according to the Cohn method or variations on the same, which has been subsequently purified by means of precipitation with PEG and anionic chromatography.

In some embodiments of the method, the initial solution of immunoglobulins has a concentration of immunoglobulins between 1 and 10 mg/ml.

In some embodiments of the method, the initial solution of immunoglobulins has a concentration of immunoglobulins between 3 and 7 mg/ml.

In some embodiments of the method, the polyether or polymer of glycol is polyethylene glycol (PEG), polypropylene glycol (PPG) or combinations of the same.

In some embodiments of the method, the concentration of PEG in the initial solution is between 2% and 6% (w/v).

In some embodiments of the method, the concentration of PEG in the initial solution is between 3% and 5% (w/v).

In some embodiments of the method, the PEG is PEG with a nominal molecular weight of 4000 Da.

In some embodiments of the method, in step a), caprylic acid or salts of the same are added to achieve a concentration between 9 mM and 15 mM.

In some embodiments of the method, in step b), the solution obtained is adjusted to a pH between 5.0 and 5.2.

In some embodiments of the method, in step b), the solution obtained is adjusted to a pH of 5.1.

In some embodiments of the method, in step c), the solution is incubated for at least 10 minutes at a temperature between 2° C. and 37° C.

In some embodiments of the method, in step c), the solution is incubated for 2 hours at a temperature between 20° C. and 30° C.

In some embodiments of the method, the initial solution of immunoglobulins has an albumin content less than or equal to 1% (w/v) with respect to the total proteins.

In some embodiments of the method, the initial solution of immunoglobulins is derived from human plasma.

In some embodiments of the method, the immunoglobulins of the initial solution of immunoglobulins are obtained by genetic recombination techniques, chemical synthesis techniques, transgenic protein production techniques, in cell cultures or combinations thereof.

In some embodiments of the method, step d) of ultrafiltration/diafiltration is carried out using a membrane of 100 kDa.

In some embodiments of the method, step d) of ultrafiltration/diafiltration is carried out in two phases:
a first phase in which the pH is adjusted to between 5.0 and 6.0 in order to reduce or eliminate most of the caprylate; and
a second phase in which the pH is adjusted to a value less than or equal to 5.0, in order to reduce or eliminate most of the polyether or polymer of glycol.

In some embodiments of the method, the second phase of step d) of ultrafiltration/diafiltration, the pH is adjusted to between 4.0 and 5.0.

In some embodiments of the method, the step of final formulation, excipients, stabilisers or combinations thereof are added, which are selected from one or more amino acids, one or more carbohydrates or polyols, or combinations of the same.

In some embodiments of the method, the final concentration of immunoglobulins is adjusted to a concentration suitable for intravenous, intramuscular or subcutaneous administration or combinations thereof.

In some embodiments, a method of viral inactivation during immunoglobulin production is provided.

In some embodiments, the method of viral inactivation comprises providing caprylic acid or salts of the same in the presence of at least one polyether or polymer of glycol for viral inactivation; and eliminating subsequent to viral inactivation said polyether or polymer of glycol and the caprylic acid or salts of the same by ultrafiltration.

DETAILED DESCRIPTION

Immunoglobulins can be administered by various routes such as the intramuscular, intravenous and subcutaneous routes, among others. Of these, it is preferable to use the intravenous route, since it offers numerous advantages, particularly greater therapeutic efficacy.

Immunoglobulins are usually purified from human plasma by using procedures based on the Cohn fractionation method (Cohn E J. et al., J Am Chem Soc, 1946, 62, 459-475), the Cohn-Oncley method (Oncley J L. et al., J Am Chem Soc, 1949, 71, 541-550) or other equivalent methods based on cold ethanol fractionation, for example the Kistler-Nitschmann method (Kistler P, Nitschmann H, 1962, 7, 414-424). Thus, using fractions rich in immunoglobulins (such as fraction II+III, or fraction II, or precipitate A, or gamma globulin GG precipitate) obtained by any of the above methods. Modifications have been introduced in order to purify the immunoglobulins more exhaustively (IgG) and make them tolerable for administration, preferably intravenously. The said modifications have been introduced, for example, in order to remove aggregates and other impurities, as well as to ensure the safety of the product. However, the addition of multiple steps to the procedure for the preparation of immunoglobulins reduces the yield of the procedure and increases manufacturing costs. Growing demand for immunoglobulin products, mainly for intravenous administration, has made yield a critical aspect in the process of producing them on an industrial scale.

Of the methods described in the prior art, the procedures for obtaining immunoglobulin compositions that are tolerable via the intravenous route include those that use the following steps: precipitation with polyethylene glycol (PEG), ion-exchange chromatography, physical/chemical methods with the capacity for viral inactivation, or treatment with enzymes and partial chemical modification of the immunoglobulin molecules.

Thus, it is necessary to ensure the safety of the product by implementing robust steps with the ability to eliminate pathogenic biological agents. The method generally used involves the use of a solvent/detergent to inactivate viruses with a lipid envelope, since this does not severely reduce the biological activity of the proteins. However, given the toxicity of solvent/detergent mixtures, this reagent must be extensively eliminated before obtaining the final product, and this increases the time required for the process and reduces the yield. The procedures described for the elimination of the said solvent/detergent are not simple and usually require the use of chromatography adsorption techniques, either directly by hydrophobic interaction or by indirect capture of the immunoglobulin in ion-exchange resins and separation of the untrapped solvent/detergent. In all cases, the processes are costly and laborious, involving significant losses of protein.

However, simpler and more efficient alternative treatments with the ability to inactivate viruses are known in the state of the art. For example, caprylic fatty acid (also known as octanoic acid) or salts of the same have been used.

In U.S. Pat. No. 4,446,134, sodium caprylate is used in combination with amino acids and heat treatment as a viral inactivation procedure in a method for the preparation of factor VIII. Although it is believed that the virucidal agent capable of disintegrating the lipid membranes is undissociated caprylic acid, the procedure that uses the said agent is commonly known as inactivation by caprylate, in accordance with the biochemical convention of denoting a solution of an acid and its ionised form with the name of the latter, i.e. caprylate.

Caprylic acid has also been used as a precipitation agent for purifying immunoglobulins (Steinbuch, M. et al., Arch. Biochem. Biophys., 1969, 134(2), 279-284). The purity of the immunoglobulins and the yield depend mainly on the concentration of caprylic acid added and the pH. Steinbuch, M. et al. also state that it is advantageous to add an effective quantity of caprylate in two different steps, with elimination of the precipitate between the two steps. This would give the procedure the ability to eliminate viruses both with and without envelopes, thanks to the distribution of non-immunoglobulin proteins in the precipitate.

Descriptions are also found in the state of the art of the combination of precipitation with caprylate followed by ion-exchange chromatography for the purification of immunoglobulins (Steinbuch, M. et al., v. supra).

European patent EP0893450 discloses a method for the purification of IgG using fraction II+III (obtained by means of procedures based on the Cohn method mentioned previously), including two anionic exchange columns in series after the steps of adding caprylate at a concentration of 15-25 mM in a double precipitation step and combining both effects of the caprylate: the reduction of non-immunoglobulin proteins by precipitation, and the capacity for viral inactivation by means of incubation. The subsequent anionic exchange steps, in addition to removing other impurities (IgM, IgA, albumin and others), are used to eliminate the caprylate, and for this reason double adsorption is required, using relatively large quantities of anionic resins.

Patent application PCT WO2005/082937 also discloses a method for the preparation of a composition that includes immunoglobulins and that comprises the steps of adding caprylate and/or heptanoate to the solution or composition that comprises immunoglobulins and, subsequently, applying the said solution in a column with anionic exchange resin.

However, the present inventors have realized that the use of caprylate at an appropriate concentration and pH (for example, pH 5.0-5.2) in order to provide the treatment with viral inactivation capacity, as has been described in the prior art, causes the formation of protein aggregates with a high molecular weight, which are partially irreversible by dilution and/or change of pH. Furthermore, these aggregates are only partially separable by filtration, and therefore require a specific subsequent step of separation, for example by means of chromatography or precipitation. The separation of these aggregates causes significant losses of protein and a reduction in the yield of the industrial process of immunoglobulin production.

In addition, the present inventors have realized that the presence of aggregates formed during the treatment with caprylate, even at very low levels, hinders the correct elimination of the caprylate by the direct application of a step of separation using an ultrafiltration membrane under optimal process conditions. These aggregates hinder or prevent the preparation of a solution of immunoglobulins at therapeutic concentrations (for example, between 5% and 20%) due to the presence of colloids (turbidity) or instability in the liquid form, thus hindering or preventing subsequent steps of the method for the preparation of immunoglobulins, such as nanofiltration and sterilising filtration.

As a consequence of the above, the present inventors have developed a method for the preparation of immunoglobulin solutions which, surprisingly, includes a caprylate treatment with the capacity for viral inactivation at a lower concentration of caprylate than that described in the prior art and which, the initial solution being suitably purified and diluted, and in the presence of at least one polyether or polymer of glycol, inhibits, prevents, avoids or does not promote the appearance of aggregates.

In addition, the present inventors have discovered that the presence of at least one polyether or polymer of glycol in the method according to the present invention does not interfere with the activity and efficacy of the caprylate in terms of its capacity for inactivating enveloped viruses.

In an additional aspect, the present inventors describe for the first time a method for obtaining immunoglobulins which, as well as including the treatment with inactivation capacity under optimal conditions, contemplates the possibility of eliminating or reducing the caprylate and polyether or polymer of glycol reagents (previously present during the said treatment) by using only the ultrafiltration technique. This ultrafiltration step makes it possible to purify and concentrate the product to levels that are tolerable for its administration, for example via the intravenous, intramuscular or subcutaneous route, without producing immunoglobulin protein aggregates in the final product. This eliminates the need to introduce additional separation steps after the treatment with caprylate, such as, for example, chromatography. Moreover, the remnant levels of polyether or polymer of glycol and caprylate after the ultrafiltration make it possible to achieve concentrations of immunoglobulins, for example IgGs, of up to 20±2%, which, if correctly formulated, do not destabilise during their conservation in liquid form.

Given the simplification of the method according to the present invention, this makes it possible to substantially improve the yield and very significantly reduce the production costs compared with the previous methods described in the prior art, without thereby compromising the level of safety or purity of the product.

Therefore, in a first aspect, the present invention relates to a method for the preparation of a solution of immunoglobulins that comprises the addition of caprylic acid or salts of the same, in the presence of at least one polyether or polymer of glycol, to the purified solution of immunoglobulins, and the subsequent elimination or reduction of the said reagents by means of ultrafiltration/diafiltration.

In an additional aspect, the present invention relates to the use of caprylic acid or salts of the same, in the presence of at least one polyether or polymer of glycol, for viral inactivation in protein production processes, and the subsequent elimination or reduction of the said reagents by means of ultrafiltration/diafiltration.

In a further aspect, the present invention relates to the implementation of a single step of ultrafiltration/diafiltration for the elimination or reduction of the levels of caprylic acid or salts of the same and/or the polyether or polymer of glycol used for viral inactivation in protein production processes.

Therefore, the present invention discloses a method for the preparation of a solution of immunoglobulins based on an initial solution of immunoglobulins with a purity greater than or equal to 96% in the presence of a polyether or polymer of glycol, characterised in that it comprises the steps of:
a) adding caprylic acid or salts of the same to the initial solution;
b) adjusting the pH of the solution obtained in step a);
c) incubating the solution obtained in step b) for the time and at the temperature necessary for the inactivation of enveloped viruses; and
d) performing a step of ultrafiltration/diafiltration on the solution obtained in step c).

The method according to the present invention may also comprise a step of final formulation of the solution obtained in step d).

In the method according to the present invention, the initial solution of immunoglobulins is derived from fraction I+II+III, fraction II+III or fraction II, obtained according to the Cohn or Cohn-Oncley method, or from precipitate A or I+A or GG, obtained according to the Kistler-Nitschmann method, or variations on the same, which have been additionally purified to obtain an IgG purity greater than or equal to 96%. Preferably, the initial solution of immunoglobulins is derived from fraction II+III obtained according to the Cohn method or variations on the same, which has been subsequently purified by means of precipitation with PEG and anionic chromatography, as described in the document EP1225180B1. According to the present patent, any of the above fractions could be subjected to a precipitation procedure using PEG, followed by filtration in order to eliminate the precipitate and an additional purification step using an ionic exchange column (for example, a column with DEAE Sepharose). In all of these cases, the initial solution of immunoglobulins is derived from human plasma.

In the most preferred embodiment, the initial solution of immunoglobulins is derived from fraction II+III obtained by procedures based on the Cohn method, which is additionally purified by any one of the methods described in the prior art to achieve an adequate level of purification to be subjected to the treatment with caprylate under the non-precipitating conditions of the present invention, i.e. a purity value greater than or equal to 96% (w/v) of IgG determined by electrophoresis in cellulose acetate, with an albumin content preferably less than or equal to 1% (w/v) with respect to the total proteins. Thus, the said initial solution of immunoglobulins is sufficiently purified, before and after the treatment with caprylate, for the route of therapeutic administration for which it is intended, so that no additional purification is required after the step with viral inactivation capacity of the present invention.

The immunoglobulins of the initial solution of the method according to the present invention can also be obtained by genetic recombination techniques, for example by expression in cell cultures; chemical synthesis techniques; or transgenic protein production techniques.

In the most preferred embodiment, the immunoglobulins mentioned in the method according to the present invention are IgGs. It is contemplated that the said IgGs may be monoclonal or polyclonal. In the most preferred embodiment, the IgGs are polyclonal.

It is contemplated that the polyethers or polymers of glycol of the present invention may be polyethers of alkane or oxides of polyalkane, also known as polyglycols, and refer, for example, to derivatives of ethyl or ethylene and propyl or propylene, better known as polyethylene glycol (PEG) or polypropylene glycol (PPG), or equivalents of the same. In addition, the said reagents must be compatible with the immunoglobulins in the sense that they do not compromise their stability or solubility and that, due to their size, they can be favourably eliminated by ultrafiltration techniques, or that, due to their lower toxicity, they are compatible with therapeutic use of the immunoglobulins.

In a preferred embodiment, the polyether or polymer of glycol is selected from polyethylene glycol (PEG), polypropylene glycol (PPG) or combinations of the same. Preferably, the polyether or polymer of glycol is PEG, more preferably a PEG with a nominal molecular weight of between 3350 Da and 4000 Da, and most preferably a PEG with a nominal molecular weight of 4000 Da.

The content of the above-mentioned polyether or polymer of glycol in the initial solution of immunoglobulins is preferably between 2% and 6% (w/v), and more preferably between 3% and 5% (w/v).

It is contemplated that it may possibly be necessary to adjust the concentration of the said polyether or polymer of glycol in the initial solution of immunoglobulins. The said adjustment of the said polyether or polymer of glycol can be effected by diluting the initial purified solution of immunoglobulins and/or by adding the same.

According to the composition of the initial solution of immunoglobulins, it is contemplated that, before step a) of the method according to the present invention, a series of steps of purification or adjustment of concentrations are carried out, such as, for example:

adjustment of the concentration of immunoglobulins to between 1 and 10 mg/ml, more preferably between 3 and 7 mg/ml. This adjustment can be effected by any of the procedures known in the state of the art, for example by dilution or concentration of the protein to the established range (determined, for example, according to total protein by optical density at 280 nm E(1%)=13.8–14.0 UA, by the Biuret method, by the Bradford method, or specifically by immunonephelometry), as the case may be. Therefore, in a preferred embodiment, the initial solution of immunoglobulins has a concentration of immunoglobulins preferably between 1 and 10 mg/ml, and more preferably between 3 and 7 mg/ml; and/or adjustment of the purity of the solution of immunoglobulins, which should preferably reach at least 96% of IgG with respect to the total proteins. This purification can be effected by techniques fully known to a person skilled in the art, such as, for example, by precipitation with PEG, and filtration and subsequent anionic exchange chromatography (DEAE Sepharose).

In step a) of the method according to the present invention, caprylic acid or salts of the same are added, preferably using a concentrated solution of the same, for example between 1.5M and 2.5M, to achieve a final concentration preferably between 9 mM and 15 mM.

In a preferred embodiment, in step b), the solution obtained is adjusted to a pH between 5.0 and 5.2, more preferably to 5.1.

In a preferred embodiment, in step c), the solution obtained is incubated for at least 10 minutes, more preferably between 1 and 2 hours, and still more preferably 2 hours. In addition, the temperature at which the said incubation is carried out is between 2° C. and 37° C., more preferably between 20° C. and 30° C.

In a preferred embodiment, before step d) of the method according to the present invention, the content of polymers or aggregates with a high molecular weight in the solution obtained in the said step c) is less than or equal to 0.2%, and more preferably less than 0.1%. This percentage of polymers or molecular aggregates of immunoglobulins with respect to the total proteins is determined by exclusion HPLC gel column according to the optical density value at 280 nm. The said percentage of polymers or molecular aggregates of immunoglobulins can be evaluated, for example, using the analysis method described in the monograph on intravenous gammaglobulin of the European Pharmacopoeia.

Preferably, the solution of immunoglobulins is clarified using depth filters before performing step d) of ultrafiltration/diafiltration.

With respect to step d), it is contemplated, preferably, that the ultrafiltration/diafiltration in the method according to the present invention has initial steps of diafiltration and concentration by reduction of volume, followed by the application of diafiltration at constant volume.

The ultrafiltration/diafiltration can be carried out on an industrial scale preferably by the method of simultaneous dialysis and concentration, reducing the volume of product and diafiltering in turn, so that the consumption of reagents is somewhat lower and the process more efficient, taking account of the fact that the concentration of proteins is optimal and preferably less than or equal to 30 mg/ml. In any event, a person skilled in the art can easily determine the most appropriate and practical way of performing this step of ultrafiltration/diafiltration, choosing from among the various operating procedures known in the state of the art (for example, dilution/concentration or diafiltration/concentration, diafiltration at constant volume, or modifications and combinations of the above).

The ultrafiltration/diafiltration membrane used in step d) of the method according to the present invention preferably consists of polysulphone, regenerated cellulose or equivalents, such as, for example, the membranes marketed under the brands Biomax® (Millipore, USA), Omega® (Pall, USA), Kvik-flow® (General Electric, USA). However, the molecular weight cut-off chosen for the membrane may vary depending on various factors, for example the manufacturer of choice. A person skilled in the art can easily determine the membrane of choice, which will be adjusted to the needs of each case depending, for example, on the concentration of caprylate and of the polyether or polymer of glycol in the solution to be processed.

Preferably, step d) of ultrafiltration/diafiltration is effected by means of a membrane with a molecular weight cut-off of less than or equal to 100 kDa, more preferably of 100 kDa.

In the most preferable embodiment, the ultrafiltration/diafiltration of step d) is performed in two phases:

a first phase in which the pH is adjusted to between 5.0 and 6.0 in order to reduce or eliminate most of the caprylate, and a second phase in which the pH is adjusted to less than 5.0, preferably to a pH of between 4.0 and 5.0, in order to reduce or eliminate most of the polyether or polymer of glycol.

In a preferred embodiment, in the first phase of the step of ultrafiltration/diafiltration, the diafiltration is performed using a diafiltration medium that comprises alkaline salts of carboxylic acid, for example acetic acid, at a concentration greater than or equal to 5 mM approximately. In the most preferable embodiment, the aforesaid diafiltration is performed using a solution of sodium acetate at a concentration greater than or equal to 5 mM adjusted to the pH mentioned above, i.e. between 5.0 and 6.0.

The number of diafiltration volumes to be performed in the first phase of step d) of ultrafiltration/diafiltration can be easily determined by a person skilled in the art according to the quantity of caprylate used initially and the acceptable final quantity. Preferably, at least three volumes of the diafiltration medium are used, the said diafiltration medium preferably being, as mentioned previously, a 5 mM solution of sodium acetate at pH 5.0-6.0. Preferably, in this first phase of the ultrafiltration/diafiltration, approximately 90% or more of the initial caprylate is eliminated, so that in this first phase the concentration of caprylate is reduced to approximately 1 mM or less.

In the second phase of step d) of ultrafiltration/diafiltration, the solution of immunoglobulins is diafiltered, preferably at constant volume.

Preferably, the diafiltration in the said second phase of the ultrafiltration/diafiltration is performed using a buffered solution that contains alkaline metal salts formed by acetate, phosphate or equivalents, or amino acids and/or polyols, for example glycine and/or sorbitol at the pH value indicated previously.

As in the case of the first phase of the diafiltration, in the second phase the number of dialysis volumes used to suitably reduce the polyether or polymer of glycol used in the method according to the present invention can be easily determined by a person skilled in the art taking account of the required reduction or elimination of the polyether or polymer of glycol. In a preferred embodiment, the quantity of buffer to be exchanged in the diafiltration of the second phase of step d) of ultrafiltration/diafiltration is equal to or greater than six volumes. In the most preferred embodiment, in the said second phase, the exchange is carried out according to the number of volumes of buffer necessary to obtain a reduction in the polyether or polymer of glycol equal to or greater than 100 times the initial content of the said polyether or polymer of glycol before beginning step d) of ultrafiltration/diafiltration.

Once the caprylate and the polyether or polymer of glycol have been reduced in step d) of ultrafiltration/diafiltration, in the final formulation step mentioned previously the solution can be adjusted to the desired final composition by adding the necessary excipients and/or stabilisers, so as to concentrate the product in order to achieve the final formulation. The addition of the excipients and/or stabilisers to be carried out after the final formulation can be effected directly by adding the said excipients and/or stabilisers in solid form or in a concentrated solution or, still more preferably, by means of diafiltration employing the necessary number of exchange volumes of a formulation solution to ensure the appropriate composition of the final product.

In another embodiment, the addition of the excipients and/or stabilisers is carried out by wholly or partially replacing the dialysis buffer solution of sodium acetate used in the second phase of step d) with a solution comprising the excipients and/or stabilisers, adjusted preferably to the same pH value of between 4.0 and 5.0 so that after the final concentration the immunoglobulin is already formulated.

A person skilled in the art knows which types of excipients and/or stabilisers must be added in order to achieve a desired stability. It is contemplated, for example, that the said excipients and/or stabilisers may be one or more amino acids, for example glycine, preferably at a concentration of between 0.2 and 0.3 M; one or more carbohydrates or polyols, for example sorbitol; or combinations of the same.

Finally, the final concentration of immunoglobulins, preferably IgGs, is adjusted to a concentration suitable for its intravenous, intramuscular or subcutaneous use, which will be known to a person skilled in the art and may, for example, be between 5% and 22% (w/v). The said concentration is effected by any procedure known in the state of the art, for example concentration by ultrafiltration. It is contemplated that if the concentration of the immunoglobulins is effected by ultrafiltration, the said concentration may be carried out using the same membrane as in the previous diafiltration. Obviously, the three diafiltrations mentioned, as well as the concentration, may also be carried out using different membranes.

The method according to the present invention also contemplates the possibility of introducing a step of nanofiltration in order to increase the safety margin of the product. There are multiple phases in the procedure in which the product can be nanofiltered with commercially available filters (for example, Planova® and Bioex® made by Asahi-Kasei, DV® and SV4® made by Pall, Virosart® made by Sartorius, Vpro® made by Millipore, or equivalents) with pore sizes from 20 nm or less and up to 50 nm, preferably with pore sizes of 20 nm or less, or even nanofilters of 15 nm can be used. The intermediate steps in which a nanofiltration step can be carried out are, for example, in the initial solution of immunoglobulins; or in the material treated with caprylate after the step of ultrafiltration/diafiltration (once the caprylate and the polyether or polymer of glycol have been reduced); or in the material after concentrating and formulating the solution of immunoglobulins, preferably IgGs (final product). A person skilled in the art will select the best option depending on, among other things, the pore size of the membrane, the filtration area required according to the time of the procedure, the volume of product to be nanofiltered, and the protein recovery.

The final product obtained by the method according to the present invention complies in full with the criteria of the European Pharmacopoeia in relation to the content of isohemagglutinins. However, the method according to the present invention also contemplates the option of including a step of selective and specific capture of anti-A and/or anti-B blood antibodies in order to maximise their reduction. This step is preferably carried out using biospecific affinity resins, as has been described in the state of the art. For example, by using biospecific affinity resins with ligands formed by trisaccharides, a significant reduction in the level of isohemagglutinins can be achieved (Spalter et al., Blood, 1999, 93, 4418-4424). This additional capture may optionally be incorporated, at the discretion of the person skilled in the art, in any step of the method of the present invention, or may be done before or after carrying out the method of the present invention.

Therefore, with respect to the method for the preparation of a solution of immunoglobulins according to the present invention, in the most preferred embodiment an initial solution of immunoglobulins with a purity greater than or equal to 96% of IgGs is used. This solution is adjusted to a concentration of IgGs preferably between 1 mg/ml and 10 mg/ml, and preferably between 3 mg/ml and 7 mg/ml, which contains (by addition in previous steps) or to which is added PEG to a concentration of 4±1% (w/v). The pH of the solution is then adjusted to between 5.0 and 5.2 with acetic acid, and sodium caprylate is added (for example, using a concentrated solution of the said sodium caprylate). In the preferred embodiment, the concentrated solution of caprylate is added to the purified solution of IgGs, slowly and with agitation. After adding all the caprylate calculated to bring the product to the final concentration of between 9 and 15 mM of caprylate, the final pH is then adjusted, if necessary, to between 5.0 and 5.2, and the solution is incubated preferably at a temperature of between 2-37° C., and more preferably at a temperature of 25±5° C., for at least 10 minutes, and preferably for between 1 and 2 hours.

Clarification is then performed using depth filters (for example, Cuno 90LA, 50LA, Seitz EK, EK-1, EKS, or equivalents).

The solution thus obtained is then processed by means of an ultrafiltration/diafiltration equipment formed by membranes comprising polysulphone, for example Biomax® made by Millipore or Omega® from Pall, preferably in the form of a stackable cassette. The solution is recirculated through each ultrafiltration/diafiltration unit, preferably at a volume of between 100-500 L/h approximately and at a temperature of 5±3° C. The pressure drop between the inlet and outlet pressures (atmospheric pressure) is preferably between 1 and 3 bar. Next, the first diafiltration phase of the step of ultrafiltration/diafiltration is begun in order to eliminate the caprylate, preferably applying an exchange of at least three volumes of buffer formed preferably by a solution of sodium acetate at a concentration equal to or greater than 5 mM and at a pH of between 5.0 and 6.0. Preferably, with each volume of buffer added or consumed, the volume of the solution of product is reduced to half of the initial volume, except for the last addition.

After the first phase of diafiltration (by dilution and concentration or equivalent), the pH of the solution obtained is adjusted to between 4.0 and 5.0 using, for example, acetic acid. Diafiltration at constant volume is then begun, preferably using six or more volumes of a buffer solution formed by sodium acetate at a concentration equal to or greater than 5 mM and at a pH of between 4.0 and 5.0.

The above-mentioned dialysis buffer solution formed by sodium acetate may optionally be wholly or partially replaced by a solution of amino acids, for example glycine at a concentration of 0.2-0.3 M, optionally combined with carbohydrates and polyols, for example sorbitol, adjusted preferably to the same pH value of between 4.0 and 5.0 so that after the final concentration the immunoglobulin is already formulated.

After applying preferably at least six volumes (more preferably between six and ten volumes) of the above-mentioned dialysis solutions at a pH of between 4.0 and 5.0, the product can be formulated, if this is not already the case, by directly adding excipient/s and/or stabiliser/s to the solution obtained, such as, for example, glycine or other amino acids, as well as carbohydrates, for example sorbitol, or a combination of the same, in the solid state or in the form of a concentrated solution of the said excipient/s and/or stabiliser/s. Next, the solution of IgGs obtained by volume reduction is concentrated to achieve the appropriate IgG concentration for intravenous, intramuscular or subcutaneous use.

The said concentrated solution, suitably adjusted with respect to the concentration of excipient/s and/or stabiliser/s and the pH, is applied by absolute filtration using filters with a pore size of 0.2 µm, and is optionally nanofiltered. Finally, the solution of IgGs is aseptically dosified in injectable preparations, ampoules, vials, bottles or other glass containers, which are then hermetically sealed. Another option is dosification in compatible rigid or flexible plastic containers, for example bags or bottles.

The dosified product goes through quarantine and visual inspection before being put into storage at a temperature between 2 and 30° C. for conservation up to at least 2 years.

Moreover, as mentioned previously, the present invention also discloses for the first time the use of caprylic acid or salts of the same in the presence of at least one polyether or polymer of glycol for viral inactivation in protein production processes, in which the said polyether or polymer of glycol and the caprylic acid or salts of the same are subsequently eliminated by means of ultrafiltration.

Preferably, the said proteins are selected from the group of proteins that comprises immunoglobulins; albumin; coagulation factors such as factor VII, factor VIII and factor IX; and von Willebrand factor. Still more preferably, the said proteins are immunoglobulins. In the most preferred embodiment, the said proteins are IgGs.

The present invention will now be described in greater detail with reference to various examples of embodiment. However, these examples are not intended to limit the scope of the present invention, but only to illustrate its description.

EXAMPLES

Example 1

Method according to the present invention for obtaining, from plasma, a solution of immunoglobulins that is virally safe, free from aggregates and with an adequate yield for industrial application.

The starting material was 16 liters of a solution of immunoglobulins, which contained IgGs as the majority protein component, obtained by the method described in European Patent EP1225180B1. In summary, the said solution was obtained by extracting gammaglobulin from fraction II+III using the Cohn method. In order to perform this extraction of gammaglobulin from fraction II+III, the said fraction was previously isolated by fractionation of human plasma using ethanol. It was then suspended in the presence of a carbohydrate, and the content of the accompanying majority proteins was reduced by precipitation with PEG-4000. Lastly, final purification of the fraction was performed by adsorption in an ion-exchange resin column (DEAE Sepharose). The column effluent thus obtained (fraction not adsorbed in the resin, i.e. the DEAE) had an electrophoretic purity in cellulose acetate (ACE) of immunoglobulins of 98±2%, a pH of 6.0, a turbidity of 2.6 Nephelometric Turbidity Units (NTU) and an IgG concentration of approximately 5 mg/ml.

The solution obtained was adjusted to a pH of 5.1 by adding acetic acid, and to a temperature of between 2 and 8° C. This solution of immunoglobulin was then brought to a final concentration of 13 mM by adding a concentrated solution of sodium caprylate.

The solution of immunoglobulins with caprylate was heated to 25° C. and incubated at this temperature for 2 hours under slow agitation. During the incubation procedure, the pH was maintained at 5.10±0.05. The turbidity of the resulting solution was 17.3 NTU.

The solution treated with caprylate was cooled to an approximate temperature of 8° C. for subsequent clarification using a depth filter (CUNO®, Ultrafilter, Denmark). Some 20 liters of filtered liquid were obtained from the said clarification (including rinsing), with an IgG concentration of approximately 4 mg/ml and a turbidity of less than 3 NTU.

The above-mentioned clarified solution was dialysed by ultrafiltration using membranes with a nominal molecular weight cut-off of 100 kDa (Biomax®, Millipore, USA). The ultrafiltration was carried out in two differentiated phases: in the first phase, the material, which had a pH of 5.1, was subjected to three steps of sequential dialysis and concentration, by means of diafiltration using a 5 mM solution of acetate adjusted to pH 5.1 and by means of concentration to approximately 30 UA. In the second phase, the solution, which had an adequate concentration of proteins, caprylate and PEG, was brought to pH 4.5±0.1 and dialysis was then begun using eight volumes of 5 mM solution of acetate at pH 4.5. Next, the product was formulated by means of dialysis using approximately 20 liters of 200 mM glycine solution at pH 4.2, and was concentrated in the same ultrafiltration unit to a value of 140.5 UA with the aim of obtaining a solution of IgGs with a concentration of 10% (w/v).

Finally, the said solution was filtered using a depth filter (CUNO®, Ultrafilter, Denmark) and absolute filters or membranes with a pore size of 0.22 µm (CVGL®, Millipore, USA; or DFL®, PALL, USA).

Table 1 shows the characterisation of the starting material, multiple intermediate products and the final product, according to the method described above. With respect to the results included in the said table, it should be noted that the turbidity was measured by nephelometry; the percentage of polymer or molecular aggregates of immunoglobulins, with respect to the total proteins detected, was determined by exclusion HPLC gel column according to the optical density value at 280 nm; the concentration of caprylate was determined using an enzymatic method by quantification of colorimetric substrate; the concentration of PEG was determined by means of an HPLC filtration gel column using a refractive index detector; and the percentage recovery of the process was calculated according to the concentration of IgG quantified by nephelometry.

The results of this example show that the treatment with caprylate of the above-mentioned purified solution does not induce any formation of immunoglobulin aggregates or other precipitates, maintaining unchanged the molecular distribution of the product. Consequently, after the treatment with caprylate, no purification steps were necessary in order to eliminate aggregates and/or precipitates. This fact greatly facilitated the production process and allowed the direct application of the material to the ultrafiltration membrane.

Thus, the subsequent ultrafiltration process satisfactorily achieved the objective of efficiently reducing the chemical reagents of the manufacturing process (i.e. PEG and caprylate), as well as allowing the subsequent formulation and concentration of the purified solution of immunoglobulin to obtain the appropriate composition for its therapeutic use.

As can be seen in Table 1, the protein recovery obtained in this case, from the starting effluent to the 10% concentrated product, was 89.4%, showing the viability of this process on an industrial scale. This recovery was greater than the value obtained by conventional methods according to the state of the art and as described in patent application PCT WO2005/073252 (70% recovery, based on a yield of 4.8 g/l compared with an initial 6.8 g/l).

Example 2

Influence of the purity of the initial solution of immunoglobulins in the treatment with caprylate.

In this example, an evaluation was made of the impact of the purity of the initial solution of immunoglobulins and the presence of accompanying proteins in the starting material subjected to the method of the present invention.

Two independent experimental test groups were created:
In group A, the starting material was the DEAE Sepharose column effluent, with an electrophoretic purity (ACE) of 98±2% IgG, i.e. the starting material described in Example 1.
In group B, the starting material, designated 4% PEG Filtrate, was obtained by the same process described in Example 1 up to the step before the DEAE Sepharosa chromatography. Thus, material B was obtained after the precipitation with PEG of the extraction suspension of fraction II+III and had an approximate electrophoretic purity (ACE) of 90% IgG.

TABLE 1

Results obtained for the starting material, multiple intermediate products and the final product in the method of Example 1.

| Sample | IgG Concentration (mg/ml) | Turbidity (NTU) | Aggregates (Polymer/Dimer) (%) | Caprylate Concentration (mM) | PEG Concentration (mg/ml) | Recovery (%) |
|---|---|---|---|---|---|---|
| Starting material (ion-exchange column effluent, already adjusted to pH 5.1) | 4.6 | 2.6 | <0.1/3.0 | 0 | 38.4 | 100 |
| Material treated with caprylate | 4.3 | 17.3 | <0.1/3.0 | 12.1 | 38.2 | 97.8 |
| Clarified material | 3.7 | 2.2 | <0.1/2.8 | 11.1 | 38.0 | 95.2 |
| Final product | 99.1 | 3.5 | <0.1/2.7 | 0.1 | 0.1 | 89.4 |

Both starting materials (group A and group B), with an equivalent PEG content of approximately 4%, were subjected to a treatment with caprylate at a concentration of 13 mM and a pH of between 5.0 and 5.2, and were purified as indicated in Example 1.

Table 2 details the main characteristics of the starting material used in both test groups (A and B, respectively), as well as those of the material produced in steps subsequent to the treatment with caprylate.

TABLE 2

Turbidity and aggregation percentage results obtained in the multiple steps of the method of the present invention for groups A and B described in Example 2.

| Starting material (group) | Purity (%) | Albumin content (mg Alb/g IgG) | Solution before treatment with caprylate | | | Solution after addition of caprylate | | Solution after incubation (2 hours at 25° C.) | |
|---|---|---|---|---|---|---|---|---|---|
| | | | O.D. 280 nm (UA) | Turbidity (NTU) | Aggregates, polymer (%) | Turbidity (NTU) | Aggregates, polymer (%) | Turbidity (NTU) | Aggregates, polymer (%) |
| Column effluent (A) | 97.9 ± 1.5 | <0.4 | 6.7 | 2.9 | <0.1 | 15.1 | <0.1 | 17 | <0.1 |
| Filtrate after treatment with PEG (B) | 90.2 ± 2.9 | 36 | 8.3 | 8 | 1.9 | 517 | 0.9 | 591 | 1.0 |

The results obtained and collected in Table 2 showed that the addition of caprylate at an effective concentration for inactivation (13 mM), to a material of lower purity (approximately 90% IgG, see group B), causes the precipitation of components of the solution, giving rise to a drastic increase in turbidity (superior a 500 NTU). Thus, the molecular distribution results for the solution showed the precipitation of part of the accompanying proteins with a high molecular weight.

The addition of caprylate, in the quantities and under the conditions described previously (13 mM of caprylate, pH between 5.0 and 5.2), to a material of low purity gave rise to a precipitated suspension that made it necessary to include additional steps of separation and purification in order to separate the proteins with a high molecular weight and precipitated aggregates. Therefore, the molecular composition of the product of group A treated with caprylate, i.e. with an aggregate content exceeding 1%, shows the non-viability of processing this product into a purified final product unless additional steps of purification or separation are included, such as steps of precipitation with PEG, chromatography or equivalent methods. Finally, this fact shows the viability of the use of caprylate as an agent with viral inactivation capacity, under non-precipitating conditions, only when it is added to a material of sufficient purity.

Example 3

Effect of the composition of the starting material on the generation of aggregates.

The objective of this experiment was to evaluate the impact of the composition of the initial solution of immunoglobulins to which the treatment with caprylate is applied.

Two independent experimental test groups were created, A and B, starting from materials of equivalent purity (97.9±1.5%) but of different composition.

In group A, the starting material was the column effluent (obtained according to the initial method described in Example 1), with a protein concentration of 5±2 mg/ml and a PEG-4000 concentration of 4±1%.

In group B, the starting material, designated Concentrated and Dialysed Effluent, was the same column effluent mentioned for group A, but after being concentrated and dialysed. Therefore, the DEAE column effluent (mentioned in Example 1 above and corresponding to group A of the present example) was subjected to an additional step of dialysis and concentration by ultrafiltration so that the PEG content was reduced by an order of approximately 6 times and the protein was concentrated to an approximate value of 4%, i.e. 40 mg/ml.

The material obtained in both experimental groups, A and B, was subjected to a treatment with caprylate at a concentration of 13 mM and a pH of between 5.0 and 5.2, and was ultrafiltered under the conditions described in Example 1 in order to obtain a product with an IgGs concentration of 10%.

Table 3 details the main characteristics of the material processed in the above-mentioned experimental groups A and B, as well as the characteristics of the material generated in the step following the treatment with caprylate and in the diafiltered and concentrated final product, for each experimental group.

TABLE 3

Results obtained for the multiple steps of the method of the present invention in groups A and B of Example 3.

| Starting material (group) | Starting material | | | Nominal caprylate (mM) | Solution after addition of caprylate | | Concentrated final product | |
|---|---|---|---|---|---|---|---|---|
| | IgG (mg/ml) | PEG (mg/ml) | Purity (%) | | Turbidity (NTU) | Aggregates, polymer (%) | Caprylate (mM) | Aggregates, polymer (%) |
| Column effluent (A) | 5 ± 2 | 40 ± 10 | 97.9 ± 1.5 | 13 | 7.0 | <0.1 | <0.1 | <0.1 |
| | | | | | 9.8 | <0.1 | 0.1 | <0.1 |
| | | | | | 11.9 | <0.1 | 0.1 | <0.1 |
| Concentrated and dialysed effluent (B) | ~40 | ~6 | 98 ± 2 | 13 | 11.9 | 0.5 | 0.3 | 0.3 |
| | | | | | 13.4 | 0.4 | 0.5 | 0.5 |
| | | | | | 10.0 | 0.3 | 0.5 | 0.4 |

As can be seen in Table 3, the results put into evidence that treatment with caprylate under the specified conditions, on a purified solution of immunoglobulin, at a concentration of 5±2 mg/ml and in the presence of a PEG concentration of 40±10 mg/ml (4±1%) (group A, column effluent), does not induce any alteration or aggregation of the solution of immunoglobulins, maintaining unchanged the molecular distribution of the product during and after the addition of the caprylate, with an undetectable proportion of aggregates of less than 0.1%.

However, when these same conditions for the treatment with caprylate were applied to a material with a low PEG content (<1%) (group B), a substantial increase in immunoglobulin aggregates was observed after the addition of caprylate. Moreover, it was not possible to eliminate this aggregate content by ultrafiltration under the conditions used, and comparable levels of polymer were measured in the final product.

Given that the main differential characteristics between the starting materials used in experimental groups A and B were the protein concentration and the PEG concentration, an additional test was performed with the aim of ascertaining the influence of each of these parameters on the subsequent treatment with caprylate.

In this experiment, the starting point was a single batch of Concentrated and Dialysed Effluent (initial material of the previous group B), which was separated into four distinct experimental groups: groups B1, B2, B3 and B4.

The material of group B1 was processed at an approximate protein concentration of 4% and an approximate PEG concentration of 0.6%.

The material of group B2 was processed at the same protein concentration of approximately 4%, but the PEG content was readjusted to a value of 4±1% (w/w).

In groups B3 and B4, the material was diluted to 0.5±0.2% of protein. With regard to the PEG content, in group B3 this was brought to a concentration of approximately 0.6% (w/w), while in group B4 the PEG content was readjusted to 4±1% (w/w).

The resulting material obtained in the four experimental groups was brought to a pH of 5.10±0.05 and a caprylate concentration of 15 mM, and was then incubated at 25° C. for 2 hours. The results obtained are shown in Table 4.

TABLE 4

Results obtained for the initial material and after incubation with caprylate for groups B1, B2, B3 and B4 of Example 3.

| Experimental group | Starting Material | | | | Solution treated with 15 mM caprylate at 25° C. for 2 hours |
|---|---|---|---|---|---|
| | IgG (mg/ml) | PEG (mg/ml) | Turbidity (NTU) | Aggregates, Polymer (%) | Aggregates, Polymer (%) |
| B1 | ~40 | ~6 | 1.6 | <0.1 | 0.5 |
| B2 | ~40 | 40 ± 6 | 2.5 | <0.1 | 0.3 |
| B3 | 5 ± 2 | ~6 | 1.3 | <0.1 | 0.5 |
| B4 | 5 ± 2 | 40 ± 6 | 1.3 | <0.1 | <0.1 |

The results shown in Table 4 show that during the treatment with caprylate under the established conditions, a PEG protective effect was observed in combination with a sufficient protein dilution. It is remarkable that when the starting material was at an approximate protein concentration of 5±2 mg/ml and a PEG concentration of 4%, undetectable values of aggregates were obtained after the treatment with caprylate (<0.1%).

Example 4

Effect of pH on the Solubility of the Solution of Immunoglobulins Treated with Caprylate It is known that the elimination of PEG in solutions of immunoglobulins, as well as the concentration of the said immunoglobulins to appropriate concentrations for their intravenous use, must take place preferably at pH values around 4.5.

Moreover, given the insolubility of caprylic acid at pH values below its pKa (4.89), in the present experiment the effect of pH on the solubility of the solution of immunoglobulins treated with caprylate was evaluated, with the aim of establishing an appropriate pH value for beginning its ultrafiltration.

To this end, a batch of column effluent obtained in accordance with the initial method detailed in Example 1 was processed to obtain the solution of immunoglobulins treated with 13 mM caprylate and clarified.

This intermediate, which constitutes the material before the ultrafiltration step, was acidified by the addition of acetic acid to take it from the pH of the treatment with caprylate (5.1) to pH values around 4.5. Subsequently, the appearance and solubility of the solution was evaluated for each of the evaluated pH values, and the generation of colloidal particles was quantified by nephelometric measurement of turbidity.

Table 5 shows the appearance and turbidity results obtained for each of the evaluated pH values.

TABLE 5

Turbidity and visual appearance results obtained for the different pH values analysed in Example 4.

| pH | Turbidity (NTU) | Visual appearance |
|---|---|---|
| 5.1 | 5.6 | Transparent |
| 5.0 | 10.0 | Transparent, small crystals |
| 4.8 | 32.5 | White, precipitated crystals |
| 4.6 | 53.0 | White, precipitated crystals |
| 4.4 | 57.1 | White, precipitated crystals |

The results obtained, as seen in Table 5, showed that when the solution of immunoglobulins treated with 13 mM caprylate was acidified to a pH of below pH 5.0, the appearance of a whitish precipitation was observed, along with a distinct increase in turbidity. This effect was very probably due to the formation of insoluble caprylic acid in colloidal form, which made it non-viable to begin the process of ultrafiltration at pH values below 5.0.

The results obtained put into evidence that when the purified solution was subjected to a treatment with caprylate, in the effective concentration range for viral inactivation (between 9-15 mM of caprylate) and under the conditions described previously, it is preferable to begin the subsequent ultrafiltration step at a pH greater than or equal to the pH of the viral inactivation treatment, i.e. 5.1, with the aim of increasing the concentration of the ionised and soluble form of caprylate and therefore facilitating its permeability through the ultrafiltration membrane.

Example 5

Effect of the acetate content in the dialysis solution on the reduction of caprylate by ultrafiltration/diafiltration.

A series of independent ultrafiltration/diafiltration processes were carried out in the presence of different concentrations of acetate in the buffer solution used for the dialysis of the product.

The starting material used, designated Concentrated and Dialysed Effluent, was the same as that of group B of Example 3. The said starting material, with an IgG purity of 98±2%, an approximate protein concentration of 40 mg/ml and an approximate PEG content of 0.6%, was subjected to a treatment with caprylate and subsequently to ultrafiltration/diafiltration using membranes with a nominal molecular weight cut-off of approximately 100 kDa.

The applied ultrafiltration/diafiltration step comprised a first phase of concentration to approximately 4% (w/v) of IgG, a second phase of dialysis using eight volumes of dialysis solution, and finally a concentration to an approximate value of 9-10% (w/v) of IgGs.

The first of the ultrafiltration/diafiltration tests was performed using water for injection, while the subsequent tests were carried out using buffer solutions with increasing concentrations of acetate, more specifically 2, 5, 20 or 50 mM of acetate respectively, and with an adjusted pH of between 5.0 and 5.5 in all cases.

TABLE 6

Results obtained for the ultrafiltration/diafiltration step using different concentrations of acetate in the dialysis buffer.

| Concentration of acetate present in the dialysis buffer (mM) | Nominal addition of caprylate (mM) | Dialysed product Caprylate in the dialysed product (mM) [1] | Permeability of the caprylate [2] |
|---|---|---|---|
| 0 | 20 | 2.3 | 13.2 |
| 2 | 13 | 0.6 | 19.3 |
| 5 | 13 | <0.2 | 32.8 |
| 20 | 13 | <0.2 | 43.3 |
| 50 | 13 | 0.2 | 45.3 |

[1] Values determined after dialysing with 8 dialysis volumes
[2] Permeability calculated by means of the following formula: Number of Dialysis Volumes = ln (Cf/Co)/(R − 1); where Cf is the concentration after dialysing with the number of dialysis volumes in question, Co is the concentration before dialysis, and R is the retention coefficient.

The results of Table 6 show that the procedure of ultrafiltration/diafiltration using membranes with a molecular weight cut-off of approximately 100 kDa, applying 8 dialysis volumes of a buffer solution with acetate, at a pH between 5.0 and 5.5 and with a minimum concentration of acetate around 5 mM and at least 50 mM, satisfactorily achieves the objective of efficiently reducing the caprylate to appropriate levels in the final concentrated product.

On the contrary, when the solution used for the dialysis was water for injection or a buffer solution with acetate levels of 2 mM, the caprylate was not effectively eliminated in the filtrate.

This puts into evidence that the method of ultrafiltration/diafiltration using a membrane with a molecular weight cut-off of approximately 100 kDa, under the conditions described previously, is effective in reducing the caprylate deriving from the previous treatment, given that correct levels of the said reagent were detected in the final concentrated product.

Example 6

Simultaneous elimination of the chemical reagents (PEG and caprylate) by means of a single step of ultrafiltration.

A batch of IgGs was processed in accordance with the method described in Example 1 to obtain the solution inactivated with caprylate and clarified. The said solution, with an approximate protein concentration of 0.5% and a pH of 5.1, was processed using an ultrafiltration/diafiltration equipment formed by polysulphone membranes of the Biomax® type (Millipore, USA) with a molecular weight cut-off of 100 kDa. The ultrafiltration/diafiltration was carried out in two differentiated phases, as described in Example 5:

In the first phase, carried out at pH 5.1, 5.6 or 5.8, the material was subjected to steps of sequential dialysis and concentration by means of diafiltration with not fewer than three volumes of buffer solution of acetate 5 mM adjusted to pH 5.1, 5.6 or 5.8, and concentrating the protein to an approximate value of 2%.

In the second phase, once the content of caprylate had been reduced to approximately one tenth, the solution was brought to a pH of 4.5±0.1 or 5.1. The product was then brought to an adequate concentration of protein and PEG to begin dialysis, and the dialysis was begun with eight volumes of buffer solution of acetate 5 mM at a pH of 4.5 or 5.1.

Finally, the product was formulated by means of dialysis with six volumes of glycine solution at a concentration of 200 mM and a pH of 4.2, and was concentrated in order to obtain a 10% solution of IgGs.

Table 7 shows the percentage of passage of PEG and caprylate obtained at the start of each of the phases of ultrafiltration/diafiltration and at different pH values:

TABLE 7

Passage of PEG and caprylate in the two phases of the ultrafiltration/diafiltration step at the different pH values analysed.

| Phase (caprylate concentration) | pH | PEG passage (%) | Caprylate passage (%) |
|---|---|---|---|
| Start of Phase I (13 mM) | 5.1 | 17 | 74 |
|  | 5.6 | 15 | 98 |
|  | 5.8 | 15 | 100 |
| Start of Phase II (1 mM) | 5.1 | 40 | 100 |
|  | 4.5 | 82 | 97 |

The results of Table 7 show that at the start of the ultrafiltration/diafiltration step, in Phase I, the caprylate showed very high passage values between pH 5.1 and pH 5.8. These values resulted in a very high reduction of caprylate during the said Phase I of the ultrafiltration/diafiltration step (a caprylate reduction of more than 10 times was obtained with respect to the initial content). On the contrary, the passage of PEG was very low (<20%) in the said Phase I, and its total elimination was practically non-viable at pH >5 in the presence of caprylate.

On the other hand, in Phase II, as can be seen in Table 7, the passage of PEG was very high at pH 4.5, with a value of 82%. In addition, it was found that during this Phase II the caprylate is also reduced, given that at the start of the phase it is present at a residual level of 1 mM, which allows the passage to be practically 100%.

Table 8 details the evolution in the concentration of protein, PEG and caprylate in each of the phases of the ultrafiltration/diafiltration step and in the final formulation step.

TABLE 8

Quantity of PEG and caprylate (measured by concentration and optical density) in the solution after the viral inactivation step, Phases I and II of the ultrafiltration/diafiltration step, formulation at pH 4.2, and in the final solution.

| Phase/Step | PEG (mg/ml) | PEG (O.D. 280 nm) | Caprylate (mM) | Caprylate (O.D. 280 nm) |
|---|---|---|---|---|
| Inactivated and clarified solution | 38 | 6.9 | 12 | 2.2 |
| Solution at the end of Phase I of the ultrafiltration/diafiltration step | 45 | 1.8 | 0.9 | 0.04 |
| Solution at the end of Phase II of the ultrafiltration/diafiltration step | 0.7 | 0.02 | 0.1 | 0.003 |
| Formulated solution at pH 4.2 | 0.1 | 0.003 | <0.1 | <0.003 |

TABLE 8-continued

Quantity of PEG and caprylate (measured by concentration and optical density) in the solution after the viral inactivation step, Phases I and II of the ultrafiltration/diafiltration step, formulation at pH 4.2, and in the final solution.

| Phase/Step | PEG (mg/ml) | PEG (O.D. 280 nm) | Caprylate (mM) | Caprylate (O.D. 280 nm) |
|---|---|---|---|---|
| Final concentrated solution | 0.1 | 0.001 | <0.1 | <0.001 |

In accordance with the PEG and caprylate values recorded at each step and phase, and considering the protein concentration at each step, the PEG reduction factor was 4 in Phase I (at pH 5.1) of the ultrafiltration/diafiltration step and 90 in Phase II (at pH 4.5) of the ultrafiltration/diafiltration step, giving a total reduction factor (Phase I and Phase II) of approximately 350 times (an initial absorbance of 6.9 compared with an absorbance of 0.02 obtained at the end of the ultrafiltration/diafiltration step).

In the case of the caprylate, the reduction factor was 55 in Phase I (at pH 5.1) of the ultrafiltration/diafiltration step and 13 in Phase II (at pH 4.5) of the ultrafiltration/diafiltration step, giving a total reduction factor (Phase I and Phase II) of approximately 700 times (an initial absorbance of 2.2 compared with an absorbance of 0.003 obtained at the end of the ultrafiltration/diafiltration step).

The results showed that the reagent with viral inactivation capacity (caprylic acid or caprylate), as well as the precipitation reagent (PEG), could be efficiently reduced by means of a single step of ultrafiltration using a membrane with a molecular weight cut-off of approximately 100 kDa, selecting the physical and chemical conditions to be applied in each phase of the ultrafiltration/diafiltration step (among others pH, protein concentration, number of dialysis volumes, dialysis buffer) and giving rise to a final product of IgGs concentrated to 10% with some remaining concentrations of both reagents suitable for intravenous use.

Example 7

Evaluation of viral inactivation capacity with caprylate in the presence of PEG.

Various independent experiments were performed, taking as the starting material the column effluent or the dialysed and concentrated effluent (obtained in accordance with Examples 1 and 3, respectively), to evaluate the capacity of caprylic acid or caprylate in the presence of PEG for eliminating or inactivating viruses with a lipid envelope.

Both materials had an immunoglobulin purity of 98±2% and a protein concentration of between 5 and 10 mg/ml, while their PEG content differed, at 40 mg/ml and 1.5 mg/ml respectively.

Viral inactivation tests were performed using the Bovine Viral Diarrhoea virus (BVDV) of the Flaviviridae family, of 40-60 nm, with a lipid envelope and an average resistance to physical and chemical agents.

In each test, the corresponding starting material was inoculated with the virus to a value less than or equal to 0.5% and subjected to a viral inactivation treatment for two hours at a temperature of 15° C. or 25° C., applying caprylate concentrations of 9 mM or 13 mM.

The quantification of the viral load of BVDV in the different samples produced was carried out by means of the TCID50 test (50% Tissue Culture Infectious Dose) using the MBDK cell line. The viral reduction factor (RF) of the viral inactivation step was determined as the quotient of the viral load detected in the inoculated starting material divided by the quantity of virus detected in the resulting sample at the end of the treatment, expressed in $\log_{10}$.

Table 9 details the characteristics of the starting material of each test, as well as the RF obtained.

TABLE 9

Viral inactivation results observed in the caprylate treatment tests with viral inoculum, in the presence or absence of PEG.

| Experimental group | Starting material | | Treatment | Caprylate | Viral reduction |
| | IgG (mg/ml) | PEG (mg/ml) | temperature (° C.) | concentration (mM) | factor (RF) |
|---|---|---|---|---|---|
| Dialysed and concentrated effluent | 10 | 1.5 | 25 | 9 | ≥4.19 |
| | | | | | ≥4.36 |
| | | | | 13 | ≥3.95 |
| | | | | | ≥4.13 |
| Column effluent | 5 | 40 | 25 | 9 | ≥4.62 |
| | | | | | ≥5.10 |
| | | | | 13 | ≥4.71 |
| | | | | | ≥4.57 |
| | | | | | ≥4.32 |
| | | | 15 | 13 | ≥4.27 |

The viral reduction results obtained in all the tests (see Table 9) show a high capacity for inactivation of BVDV in both starting materials, even for a minimal 9 mM concentration of caprylate, after treatment at different temperatures (15 and 25° C.). Furthermore, these tests showed that at each of the PEG concentrations analysed, there is no observed interference by the PEG in the viral inactivation capacity of the caprylate, given that equivalent results were obtained with both evaluated materials.

Example 8

Characterisation of the intravenous immunoglobulin solution obtained according to the production method of the present invention.

It is intended to establish the biochemical and functional characteristics of the solution of immunoglobulins with 10% (w/v) proteins obtained by the method of the present invention.

Two batches of DEAE column effluent were processed according to the method detailed in Example 1 in order to obtain the inactivated virus solution with caprylate, at an approximate scale of 200 liters of plasma.

The said solution with caprylate, once clarified, was dialysed and concentrated by ultrafiltration in differentiated phases, as described in Example 6, with the aim of achieving the elimination of the main process remnants (PEG and caprylate). Subsequently, the said purified solution, at an approximate protein concentration of 2.5%, was formulated by dialysis at constant volume for approximately 6 volumes of a buffer solution consisting of sorbitol 1% and glycine 240 mM, adjusted to pH 4.5±0.1. Finally, the said solution was concentrated by ultrafiltration and adjusted to an optical density of 140±5 UA (280 nm), equivalent to 10% (w/v) proteins, and was adjusted to a final pH of 5.25±0.25.

The product obtained (IGIV 10% (w/v)), stabilised with sorbitol and glycine, and once clarified and filtered using sterilising-grade membranes (0.22 μm), was dosified in glass bottles with chlorobutyl stoppers by determining the most relevant analytical parameters of the quality, unalterability and stability of a solution of immunoglobulin for intravenous administration. The average analytical values obtained for the two batches, as well as the specification values of the European Pharmacopoeia, are shown in Table 10.

TABLE 10

Characterisation of the solution of intravenous immunoglobulins at 10% (w/v)

| PARAMETER | PRODUCT OBTAINED BY THE METHOD OF THE INVENTION | SPECIFICATIONS (Eur. Ph.) |
|---|---|---|
| pH | 5.25 | 4.0-7.4 |
| Osmolality (mOsm/kg) | 306 | ≥240 |
| Sodium (mM) | <3.2 | n.e. |
| Turbidity (NTU) | 4.4 | n.e. |
| Molecular Distribution (%) | | |
| Polymer | <0.1 | <3.0 |
| Dimer | 7.6 | Mon. + Dim. > 90 |
| Monomer | 92.5 | |
| Fractions | <0.3 | |
| IgG subclasses (%) | | |
| $IgG_1$ | 66.7 | equivalent to plasma |
| $IgG_2$ | 27.6 | |
| $IgG_3$ | 3 | |
| $IgG_4$ | 2.7 | |
| Integrity of Fc fragment | 93 | |
| Purity profile: | | |
| Ig purity (ACE) (%) | 99.6 | ≥95 |
| IgM (mg/ml) | <0.002 | |
| NAPTT (Dil. 1/10) (s) | 308 | |
| Activated factor XI (ng/ml) | Not detected | |
| TGT FXI (nM thrombin) | <53 | |
| Isoagglutinin titre | | |
| Anti-A | Agglutination 1:16 | Agglutination ≤1:64 |
| Anti-B | Agglutination 1:16 | |
| Proteolytic activity | | |
| PKA (UI/ml) | <2 | <35 |
| ACA ($CH_{50}$/mg) | 0.6 ± 0.07 | ≤1 |

Eur. Ph.: European Pharmacopoeia; n.e.: Not Established; TGT FXI: Thrombin Generation Test (using plasma deficient in Factor IX); NAPTT PKA: Prekallikrein Activator; ACA: Anti-Complementary Activity.

The above results enhance that the product obtained is essentially unaltered as a result of the purification process of the present invention in terms of parameters such as the absence of polymer, undesirable biological activity such as PKA or ACA activity, among others, preserving some functionality characteristics intact with respect to plasma, such as proportion of IgG subclasses and Fc fragment integrity, and simultaneously showing an excellent purity profile (low titre of anti-A/anti-B isohemagglutinins, concentration of IgM, procoagulant activity, etc.).

It is concluded that the overall method of the present invention for obtaining IGIV 10% (w/v), incorporating the step of viral inactivation with caprylate in the presence of PEG and its subsequent separation, as well as the final formulation, is totally viable and scalable to the final product formulated and concentrated as IGIV 10% (w/v) protein solution, giving a final product that complies perfectly with the values established in the European Pharmacopoeia.

The stability studies carried out, which are essential for commercial viability of the product, showed the suitability of the formulations with sorbitol (to 5%), glycine (to isotonia) or a combination of both, in the pH range between 4.2 and 6.0, for stabilising 10% (w/v) solutions of intravenous immunoglobulin at ambient temperature (25° C.-30° C.) for two years.

Example 9

Applicability of the treatment with caprylate to a fraction rich in igg obtained by alternative methods.

An evaluation was made of the validity of the application with caprylate under the conditions described in the present invention, using other process intermediates obtained using alternative purification methods.

Two independent experiments were performed using as the starting material a plasma intermediate rich in IgG, the designated Suspension of Fraction II, from the Cohn-Oncley ethanol fractionation.

This intermediate was obtained by the same plasma fractionation method described in the present invention up to Fraction II+III. The procedure then continued with the alcoholic reprecipitation of the extraction suspension of fraction II+III, followed by separation of fraction III, finally obtaining fraction II with a purity greater than 96%. The suspension of the said fraction II, once purified with bentonite and dialysed with water to eliminate the alcohol content, served as the starting material for these experiments.

In the two experiments performed, the material derived from two plasma batches was separated into two different groups, A and B, according to their PEG content. In group B, the starting material was brought to a nominal PEG concentration of 40 mg/ml by adding a concentrated solution of PEG-4000.

Subsequently, both materials derived from both groups (A y B) were diluted to an approximate protein concentration of 5 mg/ml, adjusted to a pH value of 5.1, and subjected to treatment with caprylate until reaching a nominal concentration of 13 mM and a pH of between 5.0 and 5.2, as described in the method of the invention.

Table 11 details the main characteristics of the starting material used in both test groups (A and B, respectively), as well as the characteristics of the material generated after the treatment with caprylate.

TABLE 11

Main characteristics of the starting material used in groups A and B and of the final product obtained in the same. The purity of the initial solution of immunoglobulins is 99.6 ± 0.6% (n = 5 batches)

| | | Solution before treatment with caprylate | | | Solution treated with caprylate (2 hours at 25° C.) | | | |
|---|---|---|---|---|---|---|---|---|
| Experimental group | PEG (mg/ml) (1) | O.D. 280 nm (UA) | Turbidity (NTU) | Aggregates, polymer (%) | O.D. 280 nm (UA) | Turbidity (NTU) | Aggregates, polymer (%) | Caprylate (mM) (1) |
| A | <0.01 | 6.9 | 3.3 | <0.1 | 7.0 | 10.1 | 0.5 | 11.2 |
| | <0.01 | 6.9 | 3.0 | <0.1 | 7.1 | 16.5 | 1.2 | 11.2 |

TABLE 11-continued

Main characteristics of the starting material used in groups A and B and of the final product obtained in the same. The purity of the initial solution of immunoglobulins is 99.6 ± 0.6% (n = 5 batches)

| | Solution before treatment with caprylate | | | | Solution treated with caprylate (2 hours at 25° C.) | | | |
|---|---|---|---|---|---|---|---|---|
| Experimental group | PEG (mg/ml) (1) | O.D. 280 nm (UA) | Turbidity (NTU) | Aggregates, polymer (%) | O.D. 280 nm (UA) | Turbidity (NTU) | Aggregates, polymer (%) | Caprylate (mM) (1) |
| B | 34.1 | 7.1 | 2.5 | <0.1 | 7.2 | 14.5 | 0.1 | 11.9 |
| | 33.6 | 6.9 | 3.0 | <0.1 | 7.2 | 14.4 | <0.1 | 12.4 |

(1) The PEG and caprylate values correspond to the value obtained by means of analytical determination.

The results show the viability of the inactivation treatment with caprylate under the specified conditions, using an immunoglobulin solution sufficiently purified by different methods, there being no induced formation of immunoglobulin aggregates or other irreversible precipitates, which greatly facilitates the subsequent purification process.

The results show that in combination with a sufficient dilution of the protein and a sufficient degree of purity, the protective effect of PEG on the generation of immunoglobulin polymers is apparent.

This experimental example demonstrates the viability of the use of caprylate only as a reagent with viral inactivation capacity under non-precipitating conditions, and/or aggregation promoting conditions, when it is added to a material with sufficient purity and complying with the specified conditions relating to the protein and PEG concentration.

Although the invention has been presented and described with reference to embodiments of the same, it will be understood that these embodiments are not limitative of the invention, since there could be multiple variables in terms of manufacturing or other details that will be evident to a person skilled in the art after interpreting the subject matter disclosed in the present description and claims. Consequently, all variants or equivalents will be included in the scope of the present invention if they can be considered to fall within the broadest scope of the following claims.

What is claimed is:

1. A method for the preparation of a solution of immunoglobulins, wherein the method comprises the steps of:
   a) obtaining an initial solution comprising a polyether or polymer of glycol and immunoglobulins with a purity greater than or equal to 96%,
   b) adding caprylic acid or a salt thereof to the initial solution to achieve a concentration between 9 mM and 15 mM of said caprylic acid;
   c) adjusting the pH of the solution obtained in step b) to between 5.0 and 5.2;
   d) incubating the solution obtained in step c) for a time and at a temperature necessary for the inactivation of enveloped viruses; and
   e) performing a step of ultrafiltration/diafiltration on the solution obtained in step d) to obtain the solution of immunoglobulins.

2. The method according to claim 1, wherein the method also comprises a step of final formulation of the solution of immunoglobulins obtained in step e).

3. The method according to claim 2, wherein in the step of final formulation, excipients, stabilisers or combinations thereof are added, which are selected from one or more amino acids, one or more carbohydrates or polyols, or combinations of the same.

4. The method according to claim 1, wherein the initial solution of immunoglobulins is derived from fraction I+II+III, fraction II+III or fraction II, obtained according to the Cohn or Cohn-Oncley method, or from precipitate A or I+A or GG, obtained according to the Kistler-Nitschmann method, or variations thereof, which have been additionally purified to obtain a purity greater than or equal to 96% of IgG.

5. The method according to claim 4, wherein the initial solution of immunoglobulins is derived from fraction II+III obtained according to the Cohn method or variations thereof, which has been subsequently purified by means of precipitation with PEG and anionic chromatography.

6. The method according to claim 5, wherein the initial solution of immunoglobulins has a concentration of immunoglobulins between 3 and 7 mg/ml.

7. The method according to claim 1, wherein the initial solution of immunoglobulins has a concentration of immunoglobulins between 1 and 10 mg/ml.

8. The method according to claim 1, wherein the polyether or polymer of glycol is polyethylene glycol (PEG), polypropylene glycol (PPG) or combinations of the same.

9. The method according to claim 8, wherein the concentration of PEG in the initial solution is between 2% and 6% (w/v).

10. The method according to claim 8, wherein the concentration of PEG in the initial solution is between 3% and 5% (w/v).

11. The method according to claim 8, wherein the PEG is PEG with a nominal molecular weight of 4000 Da.

12. The method according to claim 1, wherein in step b), the solution obtained is adjusted to a pH of 5.1.

13. The method according to claim 12, wherein in step d), the solution is incubated for 2 hours at a temperature between 20° C. and 30° C.

14. The method according to claim 1, wherein in step d), the solution is incubated for at least 10 minutes at a temperature between 2° C. and 37° C.

15. The method according to claim 1, wherein the initial solution of immunoglobulins has an albumin content less than or equal to 1% with respect to the total proteins.

16. The method according to claim 1, wherein the initial solution of immunoglobulins is derived from human plasma.

17. The method according to claim 1, wherein the immunoglobulins of the initial solution of immunoglobulins are obtained by genetic recombination techniques, chemical synthesis techniques, transgenic protein production techniques, in cell cultures or combinations thereof.

18. The method according to claim 1, wherein step d) of ultrafiltration/diafiltration is carried out using a membrane of 100 kDa.

19. The method according to claim 1, wherein the final concentration of immunoglobulins is adjusted to a concentration suitable for intravenous, intramuscular or subcutaneous administration or combinations thereof.

20. A method for the preparation of a solution of immunoglobulins, wherein the method comprises the steps of:
   a) obtaining an initial solution comprising a polyether or polymer of glycol and immunoglobulins with a purity greater than or equal to 96%,
   b) adding caprylic acid or a salt thereof to the initial solution to achieve a concentration between 9 mM and 15 mM of said caprylic acid;
   c) adjusting the pH of the solution obtained in step b) to between 5.0 and 5.2;
   d) incubating the solution obtained in step c) for a time and at a temperature necessary for the inactivation of enveloped viruses; and
   e) performing a step of ultrafiltration/diafiltration on the solution obtained in step d).

wherein step e) of ultrafiltration/diafiltration is carried out in two phases:
   a first phase in which the pH is adjusted to between 5.0 and 6.0 in order to reduce or eliminate most of the caprylate; and
   a second phase in which the pH is adjusted to a value less than or equal to 5.0, in order to reduce or eliminate most of the polyether or polymer of glycol.

21. The method according to claim 20, wherein in the second phase of step e) of ultrafiltration/diafiltration, the pH is adjusted to between 4.0 and 5.0.

* * * * *

UNITED STATES PATENT AND TRADEMARK OFFICE
CERTIFICATE OF CORRECTION

PATENT NO. : 10,358,462 B2
APPLICATION NO. : 15/276544
DATED : July 23, 2019
INVENTOR(S) : Pere Ristol Debart Page 1 of 1

It is certified that error appears in the above-identified patent and that said Letters Patent is hereby corrected as shown below:

On the Title Page

Item [56], Column 2, Line 14, under Other Publications, change "methodoloy" to --methodology--.

In the Specification

Column 8, Line 23, change "Kvik-" to --Kvick--.

Column 14, Line 18, change "Sepharosa" to --Sepharose--.

Column 17, Line 40, change "Caprylate" to --Caprylate.--.

Column 21, Line 67, change "MBDK" to --MDBK--.

Column 24, Line 19, change "igg" to --IgG--.

Column 24, Lines 44 and 45, change "(A y B)" to --(A and B)--.

In the Claims

Column 27, Line 19, Claim 20, change "d)." to --d);--.

Signed and Sealed this
Seventeenth Day of December, 2019

Andrei Iancu
*Director of the United States Patent and Trademark Office*